United States Patent
Yoo (10) Patent No.: US 6,626,494 B2
(45) Date of Patent: Sep. 30, 2003

(54) CHAIR AND METHOD FOR CORRECTING AN IMPROPER ALIGNMENT OF SPINAL VERTEBRAE

(76) Inventor: Han-Keel Yoo, 6-903 Jamwon Hansin Apt., Jamwon-Dong, Seocho-Gu, Seoul (KR)

( * ) Notice: Subject to any disclaimer, the term of this patent is extended or adjusted under 35 U.S.C. 154(b) by 0 days.

(21) Appl. No.: 09/955,134

(22) Filed: Sep. 19, 2001

(65) Prior Publication Data

US 2002/0033626 A1 Mar. 21, 2002

(30) Foreign Application Priority Data

Sep. 19, 2000 (KR) .......................... 2000-26322
Sep. 19, 2000 (KR) .......................... 2000-55024

(51) Int. Cl.$^7$ .................................. A47C 7/44
(52) U.S. Cl. ................... 297/296; 297/353; 297/391; 297/410; 297/314; 297/313; 297/284.4; 297/284.7
(58) Field of Search .................. 297/353, 284.4, 297/409, 408, 410, 406, 314, 391, 354.12, 357, 368, 369, 338, 217.3, 452.33, 452.29, 230.12, 461, 452.41, 451.1, 451.5, 451.4, 185, 296, 301.1

(56) References Cited

U.S. PATENT DOCUMENTS

| | | | | |
|---|---|---|---|---|
| RE8,389 E | * | 8/1878 | Whitcomb | 297/314 |
| 530,880 A | * | 12/1894 | Briggs, Jr. | 297/296 |
| 929,272 A | * | 7/1909 | Baron | 248/583 |
| 1,029,315 A | * | 6/1912 | Poll | 297/408 |
| 2,439,869 A | * | 4/1948 | Sharp | 248/161 |
| 3,059,971 A | * | 10/1962 | Becker | 297/353 |
| D198,449 S | * | 6/1964 | Kerr | 297/391 |
| 4,153,293 A | * | 5/1979 | Sheldon | 297/230.14 |
| 4,191,422 A | * | 3/1980 | Inasawa et al. | 297/391 |
| 4,285,081 A | * | 8/1981 | Price | 5/637 |
| 4,761,034 A | * | 8/1988 | Saito | 297/408 |
| 4,793,655 A | * | 12/1988 | Kvalheim et al. | 297/118 |
| D306,245 S | * | 2/1990 | Akhtarekhavari | 297/391 |
| 5,711,576 A | * | 1/1998 | Olson et al. | 297/353 |
| 5,803,542 A | * | 9/1998 | Insausti | 297/230.12 |
| 5,897,166 A | * | 4/1999 | Tsai | 297/353 |
| 5,918,941 A | * | 7/1999 | Kigel | 297/353 |
| 5,967,613 A | * | 10/1999 | McKeever | 297/397 |
| 6,053,880 A | * | 4/2000 | Sleichter, III | 297/217.3 |
| 6,279,998 B1 | * | 8/2001 | Chu et al. | 297/338 |
| 6,357,827 B1 | * | 3/2002 | Brightbill et al. | 297/233 |
| 6,394,547 B1 | * | 5/2002 | Vik | 297/298 |
| 6,419,318 B1 | * | 7/2002 | Albright | 297/284.4 |

* cited by examiner

*Primary Examiner*—Peter M. Cuomo
*Assistant Examiner*—Stephen D'Adamo
(74) *Attorney, Agent, or Firm*—Foley & Lardner (57) ABSTRACT

Disclosed is a chair and a method using the chair, which can be not only used easily and comfortably but also utilized in treating an improper alignment of spinal vertebrae. The chair has a seat assembly for seating the user on the seat assembly, the seat assembly being operated by the user in such a manner as that the user can adjust a height of the seat assembly; a backrest assembly for supporting a back of the user, the backrest assembly being operated separately from the seat assembly by the user in such a manner that the user can adjust a height of the backrest assembly; a headrest assembly for resting a head of the user on the headrest assembly, the headrest assembly being assembled with the backrest assembly; and a backrest frame for supporting the backrest assembly and the headrest assembly, the backrest frame being fixed to the seat assembly, the backrest assembly moving along the backrest frame when the height of the backrest assembly is adjusted.

21 Claims, 11 Drawing Sheets

CHAIR AND METHOD FOR CORRECTING AN IMPROPER ALIGNMENT OF SPINAL VERTEBRAE

BACKGROUND OF THE INVENTION

1. Field of the Invention

The present invention relates to a chair for correcting an improper alignment of spinal vertebrae and a method for correcting an improper alignment of spinal vertebrae by means of the chair, which can be not only used easily and comfortably but also utilized in treating an improper alignment of spinal vertebrae of the user. By repeatedly using the chair and the method of the invention, gaps between the user's spinal vertebrae are repeatedly enlarged and contracted by themselves, so that not only pain due to compression of paraspinal nerves can be naturally reduced and tension of paraspinal muscles can be relieved, but also a misalignment of the spinal vertebrae can be corrected, that is, a herniation of intervertebral disk can be prevented and treated.

2. Description of the Prior Art

A spine is a pillar of a human body and contains a spinal marrow connected to a human brain so as to control and regulate all the functions of the human body. The spine supports the weight of the human body and protects the spinal marrow, which is an organ for transferring orders from the brain to each part of the human body.

Therefore, it is essential for an individual in keeping himself or herself in good health to maintain twenty-four spinal vertebrae protecting such spinal marrow as described above, a pelvis, and a skull in their correct positions. The spine consisting of the twenty-four vertebrae connected in series also functions as an intermediate bridge for connecting the pelvis and the skull with each other.

When the spinal vertebrae are in their original correct positions, the spinal marrow and the vertebral nerves can work without any hindrance. On the contrary, when the spinal vertebrae are out of their original positions, the vertebral nerves, which has to pass between the spinal vertebrae, starts to be compressed and thereby various nervous systems starts to be disabled. Such hindrances in the nervous systems deteriorate functions of related organs of the human body and their immunological competence, which thereby may cause a severe disease.

A severe disease may be caused by various reasons such as wrong postures, wrong habit of living, improper exercise, stress, accident, and heredity. Among those reasons, a misalignment of the spinal vertebrae due to such reasons as severe accident and heredity may make an individual to be physically handicapped. However, even a slight misalignment of the spinal vertebrae may cause various diseases.

A human spine is shaped like a large letter "S" in a view from the lateral side, which functions as a great leaf spring capable of well distributing the weight of the human body. In a view of the front side, the human spine extends in a straight line without any curve, so as to maintain the balance of the human body well.

When such a curve and a straight line by the spine are distorted, the weight of the human body may press the human body itself as formidable stress. Further, the distortion of the original lines by the spine may slightly displace the spinal vertebrae from their original positions, and then the muscles rigidified for supporting the displaced spinal vertebrae and the weight of the human body press the vertebral nerves and the paravertebral nerves, thereby causing greater pain, which applies a stronger pressure on the nerves again, resulting in a vicious circle.

In the meantime, a large number of individuals suffer from chronic back pain. Many of these individuals acquire this problem due to prolonged exposure to incorrect posture associated with occupational activities. That is, individuals such as students and office workers spend most of their time with being seated in chairs, and loads to their spines are increased by about one and a half times when they are seated in chairs in comparison with the case where they stand. Further, since a weight of an individual's upper body is delivered to the individual's spine and pelvis when the individual has a seated posture, muscular stress is concentrated on the individual's spine, pelvis, and muscles surrounding the spine and pelvis to thereby provide the individual with fatigue and pain, when the individual is seated in a chair for a long time. Moreover, the individual may get a so-called spine disk disease, namely a herniation of intervertebral disk, when the individual takes an improper posture for a long time due to his or her wrong sitting habit or a wrongly designed chair.

In general, when an individual has a misalignment of the spine, he or she is subjected to an oriental treatment utilizing an oriental therapeutic needle, a physical treatment, or a finger-pressure therapy, in which the individual's muscles near the misaligned vertebrae are pressed by a curer's fingers.

Further, among existing systems for correcting a patient's spinal misalignment there is a system utilizing a method, in which the patient is hung upside down so that the patient's spinal vertebrae are elongated, thereby being correctly aligned. In this system, although the patient's paraspinal muscles or tissues are elongated, the elongation of the very spinal vertebrae is small and it is difficult to maintain the patient's physiological curvature, an S-shaped curvature, so that it is difficult to achieve a good treating effect. Moreover, this method may be very dangerous especially to a patient with hypertension.

Also, to those related in the art is a vertebral traction bed for correcting a patient's spinal misalignment, which has a horizontal mat. In the traction bed, in state that a patient is lying on the bed, the patient's spinal vertebrae including cervical vertebrae are drawn in the patient's longitudinal direction, or moreover the patient's upper and lower bodies are swayed in opposite directions while the cervical and spinal vertebrae are drawn, gaps between the spinal vertebrae are enlarged so that herniated spinal marrow is restored to its original position. However, in this traction bed, it is also difficult to maintain the patient's physiological curvature. Moreover, since the spinal vertebrae are forcedly drawn, the paraspinal muscles are unnecessarily stressed, causing harmful effect, and the elongation of the spinal vertebrae shows an insignificant degree. Especially, in a case where the patient's spinal vertebrae are drawn by means of a belt fastened around the patient's jaw, the patient may get a ruptured cervical disk. Therefore, such a method has to be inhibited. Further, since the vertebral traction bed is too expensive, it is not used in general but is usually used in hospitals specialized in spinal treatment.

SUMMARY OF THE INVENTION

Accordingly, the present invention has been made in an effort to solve the problems occurring in the related art, and it is an object of the present invention to provide a chair for correcting an improper alignment of spinal vertebrae and a method for correcting an improper alignment of spinal vertebrae by means of the chair, which not only can be used easily and comfortably but also can be utilized in treating an improper alignment of spinal vertebrae of the user.

It is another object of the present invention to provide a chair for correcting an improper alignment of spinal vertebrae and a method for correcting an improper alignment of spinal vertebrae by means of the chair, by which a user can treat the improper alignment of spinal vertebrae by himself or herself with a simple operation without any additional apparatus.

It is another object of the present invention to provide a chair for correcting an improper alignment of spinal vertebrae and a method for correcting an improper alignment of spinal vertebrae by means of the chair, in which a user's scapular muscles can be stimulated to be tenderized, so that the pain at the user's cervical portion can be soothed, while the physiological curvature of the user's scapular portion is maintained.

In accordance with one aspect, the present invention provides a chair for correcting an improper alignment of spinal vertebrae of a user of the chair, the chair comprising: a seat assembly for seating the user on the seat assembly, the seat assembly being operated by the user in such a manner as that the user can adjust a height of the seat assembly; a backrest assembly for supporting a back of the user, the backrest assembly being operated separately from the seat assembly by the user in such a manner that the user can adjust a height of the backrest assembly; a headrest assembly for resting a head of the user on the headrest assembly, the headrest assembly being assembled with the backrest assembly; and a backrest frame for supporting the backrest assembly and the headrest assembly, the backrest frame being fixed to the seat assembly, the backrest assembly moving along the backrest frame when the height of the backrest assembly is adjusted.

Preferably, the seat assembly may comprise supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle.

Also, it is preferred that the backrest frame includes a horizontal lower section, a vertical upper section, and a curved elastic section interconnecting the horizontal lower section and the vertical upper section, which are integrated as a single elastic member, the horizontal lower section having one end fixed to the base cylinder.

Also, the backrest assembly includes a backrest and a backrest-elevating system for moving the backrest up and down along the vertical upper section of the backrest frame.

Moreover, the headrest assembly may include a headrest, a supporting plate, a carrier plate, a headrest frame, and a headrest frame holding bracket, the headrest frame holding bracket being fixed to a rear surface of the backrest, the headrest frame being held by and extends vertically upward from the headrest frame holding bracket, the supporting plate being fixed to an upper end of the headrest frame, and the carrier plate being disposed on the supporting plate and fixed to the headrest so as to carry the headrest the carrier plate being capable of sliding forward and backward on the supporting plate.

More preferably, the headrest has a head-resting wall, two neck-holding protrusions protruding forward from lower end portions of the head-resting wall, and a neck-seating portion formed between the two neck-holding protrusions. The neck-seating portion has such a width as to as to enable a lower portion of the user's head to be caught by the two neck-holding protrusions when the head and a neck of the user have respectively been seated on the head-resting wall and the neck-seating portion.

In accordance with another aspect, the present invention provides a method for correcting an improper alignment of spinal vertebrae of a user of the chair, the chair including a seat assembly, a backrest assembly whose height can be adjusted separately from the seat assembly, a headrest assembly assembled with the backrest assembly, and a backrest frame for supporting the backrest assembly and the headrest assembly, the seat assembly including supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle, the backrest frame being fixed to the seat assembly, the backrest assembly moving along the backrest frame when the height of the backrest assembly is adjusted, the backrest assembly having a backrest and a backrest-elevating system, the headrest assembly having a headrest, which includes a head-resting wall, two neck-holding protrusions protruding forward from lower end portions of the head-resting wall, and a neck-seating portion formed between the two neck-holding protrusions, the method comprising the steps of: (1) seating the user on the seat; (2) operating the handle and the backrest-elevating system to respectively adjust heights of the seat and the backrest assembly so that a back of the user comes into tight contact with the backrest of the backrest assembly; (3) inserting a neck of the user between the neck-holding protrusions, so that the head of the user is seated on the head-resting wall; and (4) operating the driving handle again to eliminate an upward pressure by the seat-elevating rod for supporting the seat.

Preferably, the method further comprises a step of adjusting a frontward location and an inclination of the headrest.

According to the present invention, the user can have a distinctive spinal groove representing a strong and healthy spine, which extends along the human spine and is formed on a human back by the human spine and the paraspinal muscles.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF THE PREFERRED EMBODIMENTS

The above and other objects, characteristics, and advantages of the present invention will be apparent from the following description along with the accompanying drawings.

Referring to FIGS. 1A to 1D, which show a chair for correcting an improper alignment of spinal vertebrae according to an embodiment of the present invention, the chair includes a seat assembly 100, a backrest assembly 200, a headrest assembly 300, and a backrest frame 11 connected to the seat assembly 100 and supporting the backrest assembly 200 and the headrest assembly 300.

The seat assembly 100 includes supporting legs 1 for generally supporting the seat assembly 100, a base cylinder 3 integrated with and supported by the supporting legs 1, a seat-elevating rod 4 movably inserted in the base cylinder 3, and a seat 7 assembled with and supported by the seat-elevating rod 4. The seat-elevating rod 4 is elevated by an actuating system (not shown) housed in the base cylinder 3, which is operated by a driving handle 5. At a lower surface of the seat 7 is provided a seat bracket 6, which is fixed to the upper end of the seat-elevating rod 4. Therefore, when a user of the chair operates the driving handle 5 without pressing the seat 7 downward, the seat-elevating rod 4 together with the seat 7 is moved upward by the actuating system housed in the base cylinder 3. On the other hand, when the user seats on the seat 7 while operating the driving handle 5, the seat 7 is rapidly lowered due to the user's weight. When the driving handle 5 is restored to its original state of non-operation, the seat 7 is maintained at the height at the very time when the operation of the driving handle 5 is stopped. The actuating system may employ various operation methods, for example, the actuating system may be operated by gaseous, hydraulic, or electromotive force.

Meanwhile, the backrest frame 11 includes a horizontal lower section 112, a vertical upper section 114, and a curved elastic section 33 interconnecting the horizontal lower section 112 and the vertical upper section 114, which are integrated as a single elastic member. The horizontal lower section 112 extends horizontally from a lower end of the curved elastic section 33 and a distal end of the horizontal lower section 112 is fixed to the base cylinder 3 by means of various ways such as welding. Of course, according to another embodiment of the present invention, the backrest frame 11 may be integrally formed together with the base cylinder 3. The vertical upper section 114 extends vertically upward from the curved elastic section 33. When the user leans against a backrest, which will be described later, the curved elastic section 33 is elastically widen to provide a user with a comfort feeling.

The backrest assembly 200 includes a backrest 10, and a lower backrest bracket 9 and an upper backrest bracket 29 respectively fixed at lower and upper portions of a rear surface of the backrest 10. The vertical upper section 114 of the backrest frame 11 is fitted through the lower backrest bracket 9 and the upper backrest bracket 29 in such a manner as that the backrest 10 together with the lower backrest bracket 9 and the upper backrest bracket 29 can be moved up and down along the vertical upper section 114. At the lower backrest bracket 9 is provided a backrest-elevating system 15, which can move the backrest 10 with the lower backrest bracket 9 and the upper backrest bracket 29 up and down along the vertical upper section 114. Also, a button 8 for operating the backrest-elevating system 15 is disposed at the lower backrest bracket 9. The backrest 10 has a curved shape like the letter "C" in a view from its lateral side, which is complementary to a human spinal curvature and thereby is capable of fitly supporting a human back. Also, the backrest 10 has a contour of a straight line at a portion thereof, against which the user's waist leans, in a view from above, so as to maximize the portion, with which the user's waist is in contact. Further, the backrest 10 has a vertical elongated hole 13 formed through a central portion of the backrest 10, with which a central portion of the human back is to be in contact.

Figure 3A:
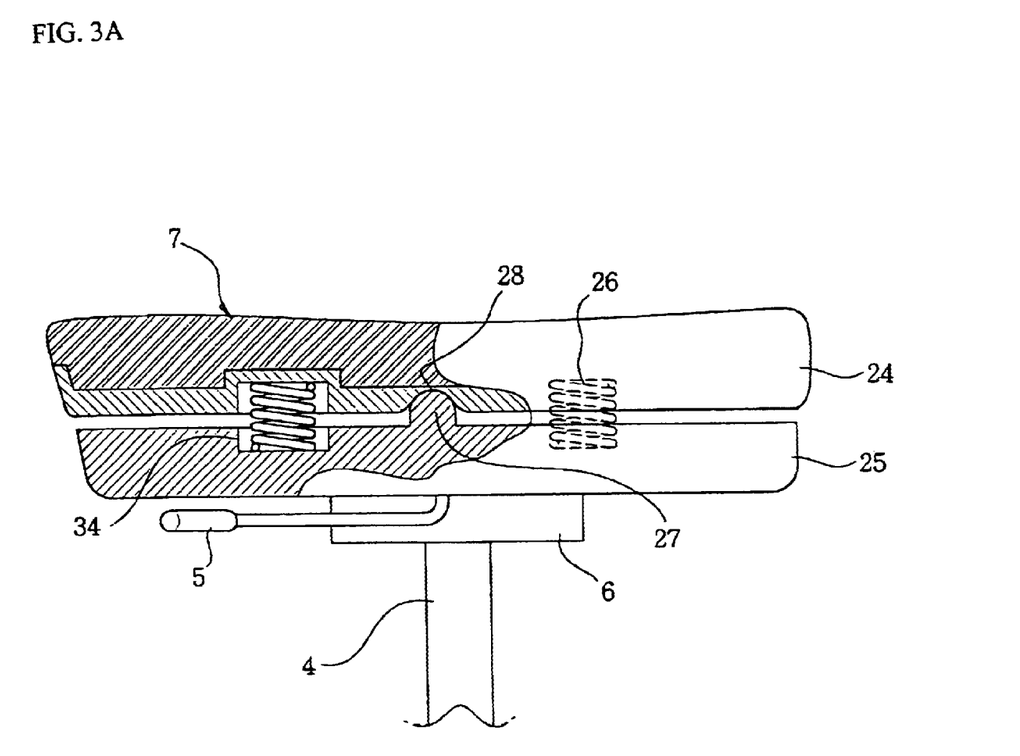
FIG. 3A is a detailed sectional view of a seat employed in the chair shown in FIG. 1A.
Figure 3B:
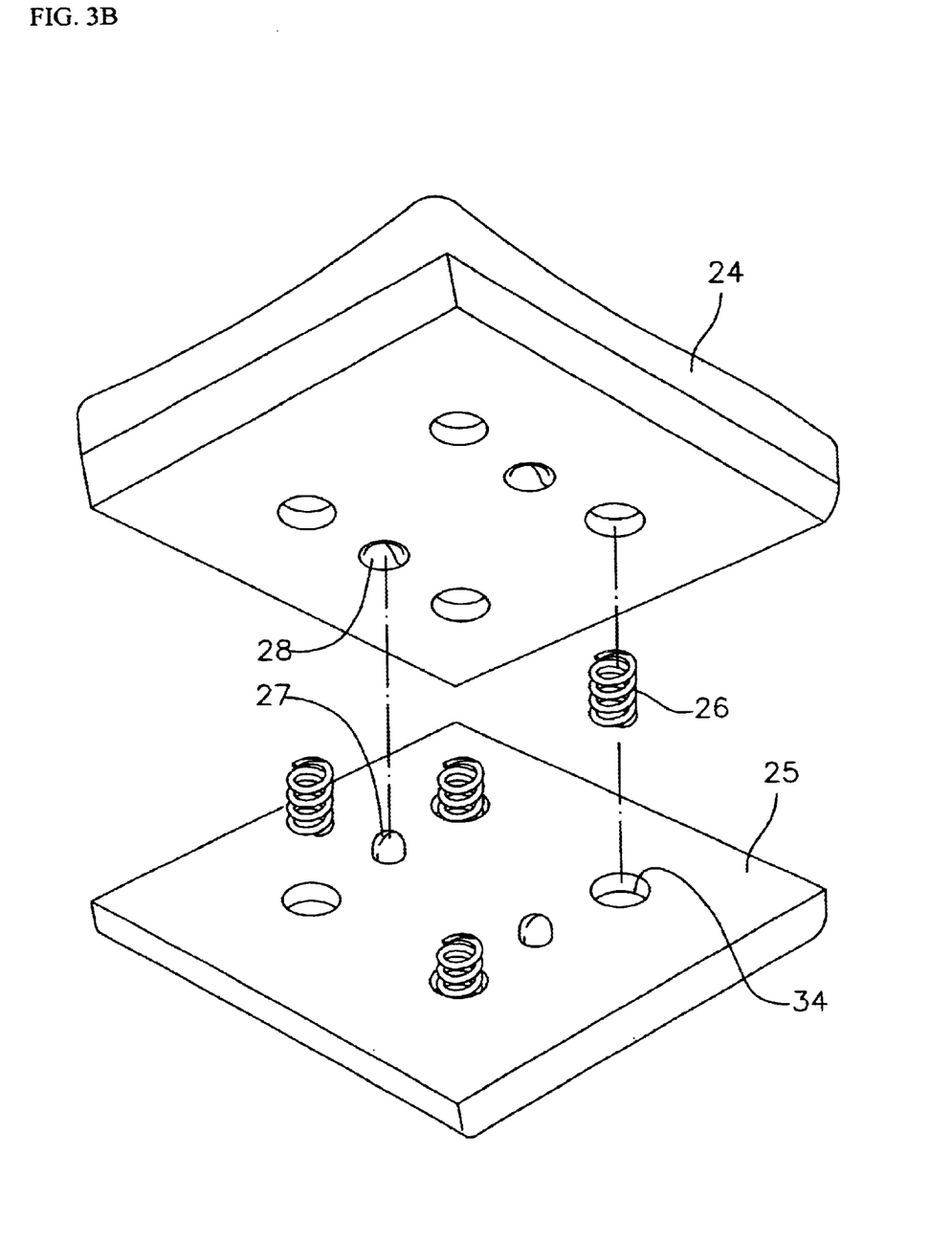
Figure 4:
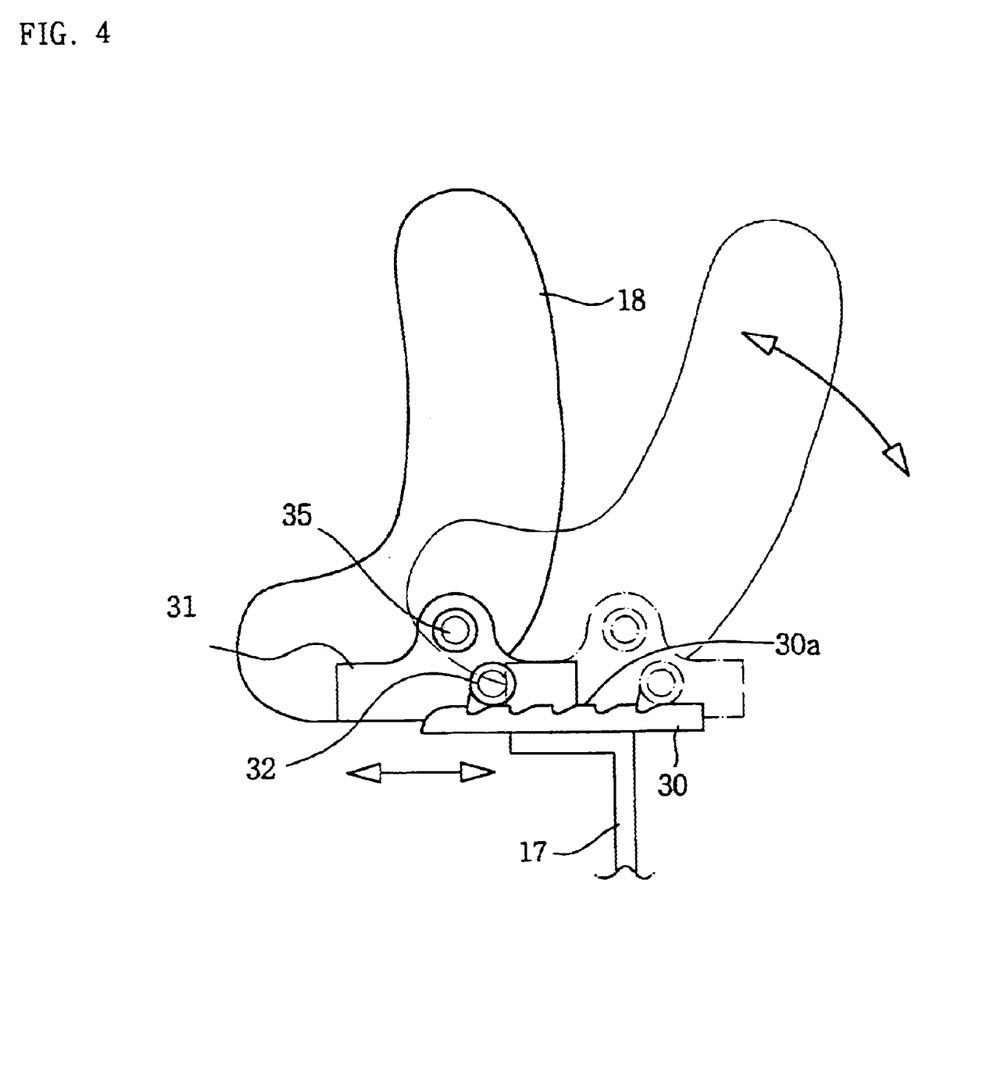
FIG. 4 is a side view of a headrest assembly employed in the chair shown in FIG. 1A.

Referring to FIG. 3A, the seat 7 includes an upper seat plate 24 and a lower seat plate 25 assembled with each other. A pair of assembling grooves 28 (only one of the pair shown) are formed at central portions of the upper seat plate 24, and a pair of assembling protuberances 27 (only one of the pair shown) are formed at central portions of the lower seat plate 25. The assembling grooves 28 and the assembling protuberances 27 are engaged with each other, so as to space the upper seat plate 24 and the lower seat plate 25 from each other with a predetermined interval. Further, spring recesses 34 are formed at four corners of a lower surface of the upper seat plate 24 and at four corners of an upper surface of the lower seat plate 25, and four first springs 26 are inserted each in each pair of the spring recesses 34 opposed to each other. Therefore, when the user of the chair inclines his or her body in one direction he or she wants, the upper seat plate 24 is elastically inclined in the direction corresponding to the inclination of the user's body.

Referring to FIGS. 1A to 1D, and 4, the headrest assembly 300 includes a headrest 18, a supporting plate 30, a carrier plate 31, a headrest frame 17, and a headrest frame holding bracket 16. The headrest frame holding bracket 16 is fixed to the rear surface of the backrest 10, and the headrest frame 17 is fixedly held by and extends vertically upward from the headrest frame holding bracket 16. The supporting plate 30 is fixed to the upper end of the headrest frame 17, and the carrier plate 31 is slidably disposed on the supporting plate 30 and is fixed to the headrest 18 so as to carry the headrest 18. The supporting plate 30 has a serrated upper surface 30a, and the carrier plate 31 has a carrier plate adjusting lever 32, which can be operated to be engaged with each tooth of the serrated upper surface 30a of the supporting plate 30 so as to adjust the location of the carrier plate 31 carrying the headrest 18. That is, the carrier plate 31 can be moved forward and backward and then be firmly held in its location, as shown by the solid and dotted lines in FIG. 4. In this case, the carrier plate adjusting lever 32 can be pivoted or laterally pulled and pushed when it is engaged with and disengaged from the tooth of the serrated upper surface 30a. Therefore, according to the user's physical dimensions or the user's necessity, the location of the headrest 18 can be adjusted forward or backward by means of the supporting plate 30, the carrier plate 31, and the carrier plate adjusting lever 32.

Figure 1A:
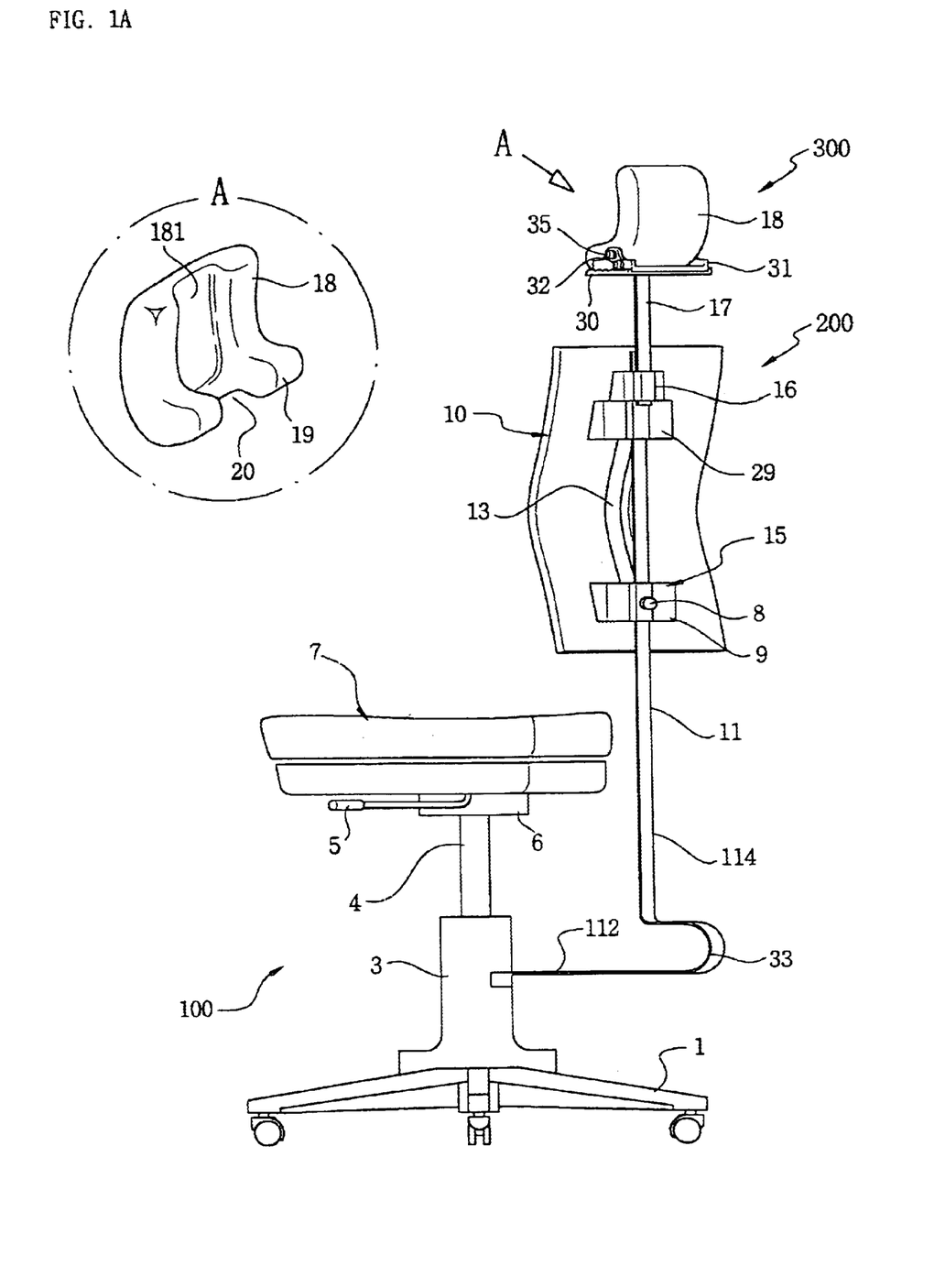
FIG. 1A is a side elevation of a chair for correcting an improper alignment of spinal vertebrae according to an embodiment of the present invention, in which a backrest assembly and a headrest assembly are shown in a perspective view.
Figure 1B:
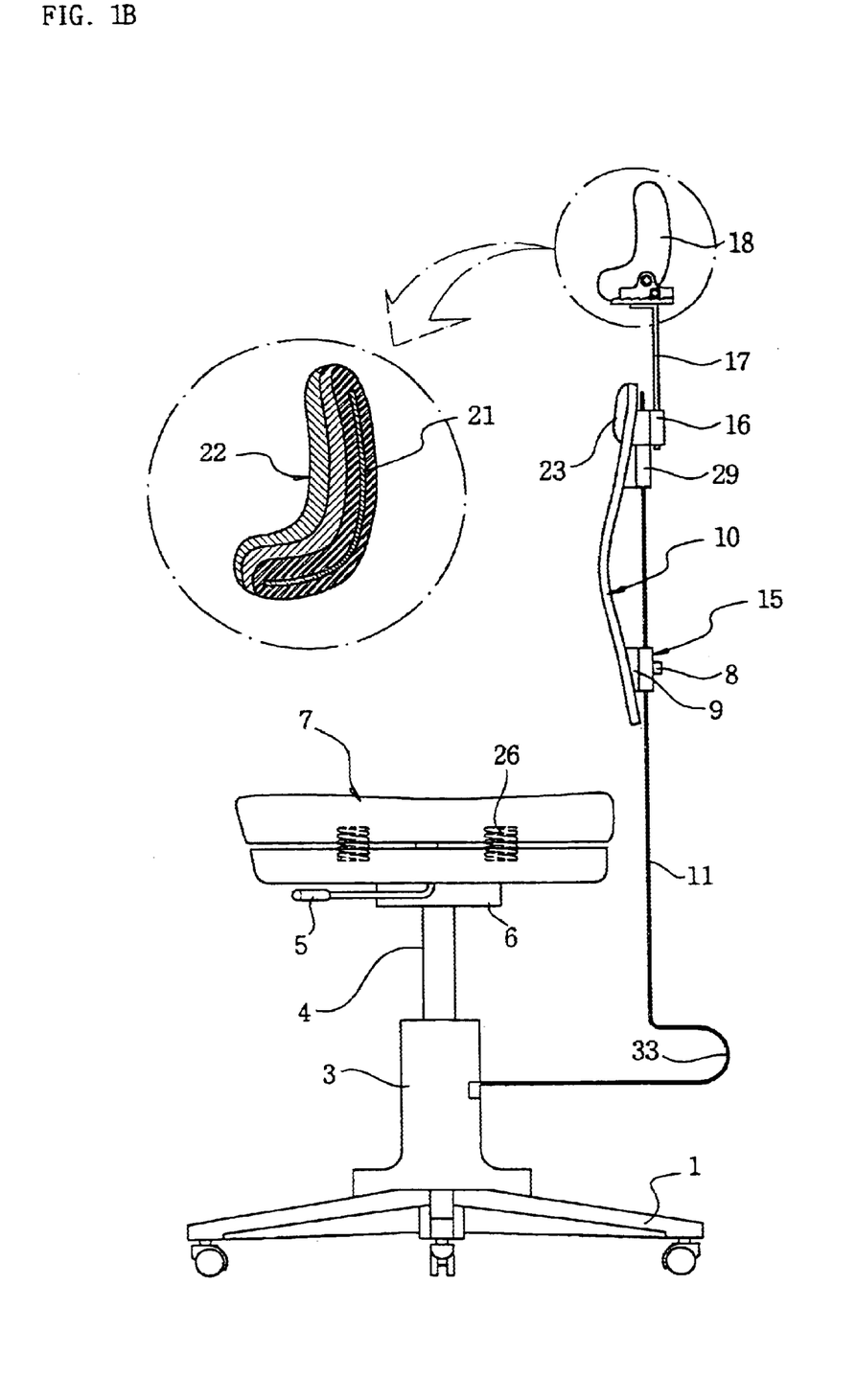
FIGS. 1B to 1D are side, rear, and front elevations of the chair shown in FIG. 1A.
Figure 1C:
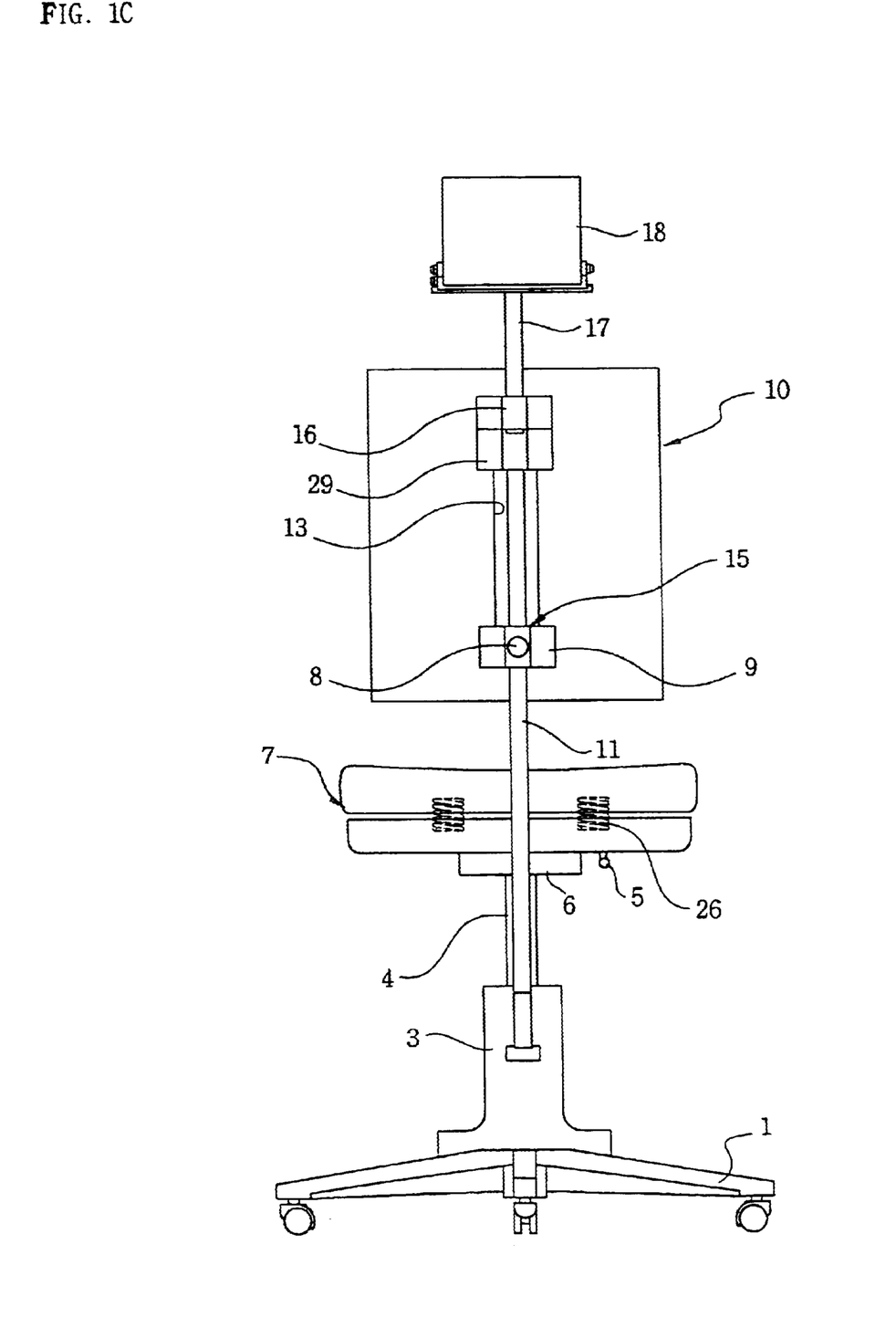

As shown in detail in the enlarged view designated by the circle A in FIG. 1A, the headrest 18 has a head-resting wall 181, two neck-holding protrusions 19 protruding forward from lower end portions of the head-resting wall 181, and a neck-seating portion 20 formed between the two neck-holding protrusions 19. It is preferred that the width of the neck-seating portion 20, the interval between the two neck-holding protrusions 19, has such a value as to enable a lower portion of the user's head to be caught by the two neck-holding protrusions 19 when the user's head and neck have respectively been seated on the head-resting wall 181 and the neck-seating portion 20.

Referring again to FIG. 4, the carrier plate 31 further has a headrest pivoting mechanism 35, which is fixed to the headrest 18 in such a manner as to pivot the headrest 18 as shown by the solid and dotted lines in FIG. 4. Therefore, the user can choose an inclined angle of his or her head, at which the user feels comfortable, by properly pivoting the headrest 18 by means of the headrest pivoting mechanism 35, when the user lays his or her head on the headrest 18. When the headrest 18 is pivoted backward as shown by the dotted line after the user's head and neck are respectively seated on the head-resting wall 181 and the neck-seating portion 20, the neck-seating portion 20 comfortably supports the user's neck while maintaining the physiological curvature of the user's neck and provides the user with a feeling that the user's neck is slightly pulled upward.

In order to ensure those functions of the headrest 18 as described above, it is preferred that the headrest 18 is made from three kinds of materials. That is, as shown by an enlarged view circled in FIG. 1B, the headrest 18 has a base plate 21 made from hard material, and three laminated layers of cushions 22 surrounding the base plate 21 are made from soft materials. Moreover, it is preferred that the more outer the layer is disposed, the softer it is.

Figure 1D:
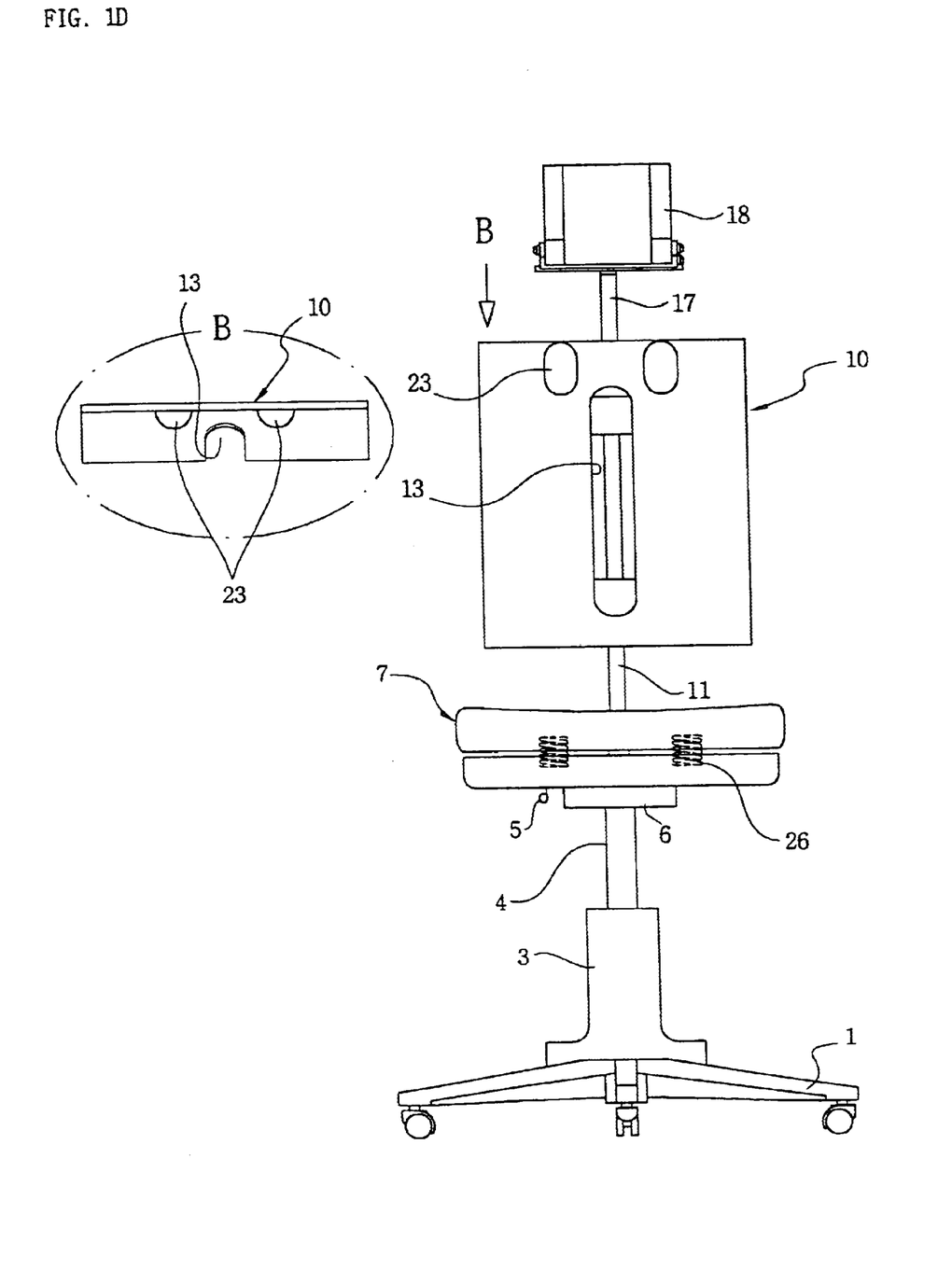
Figure 1E:
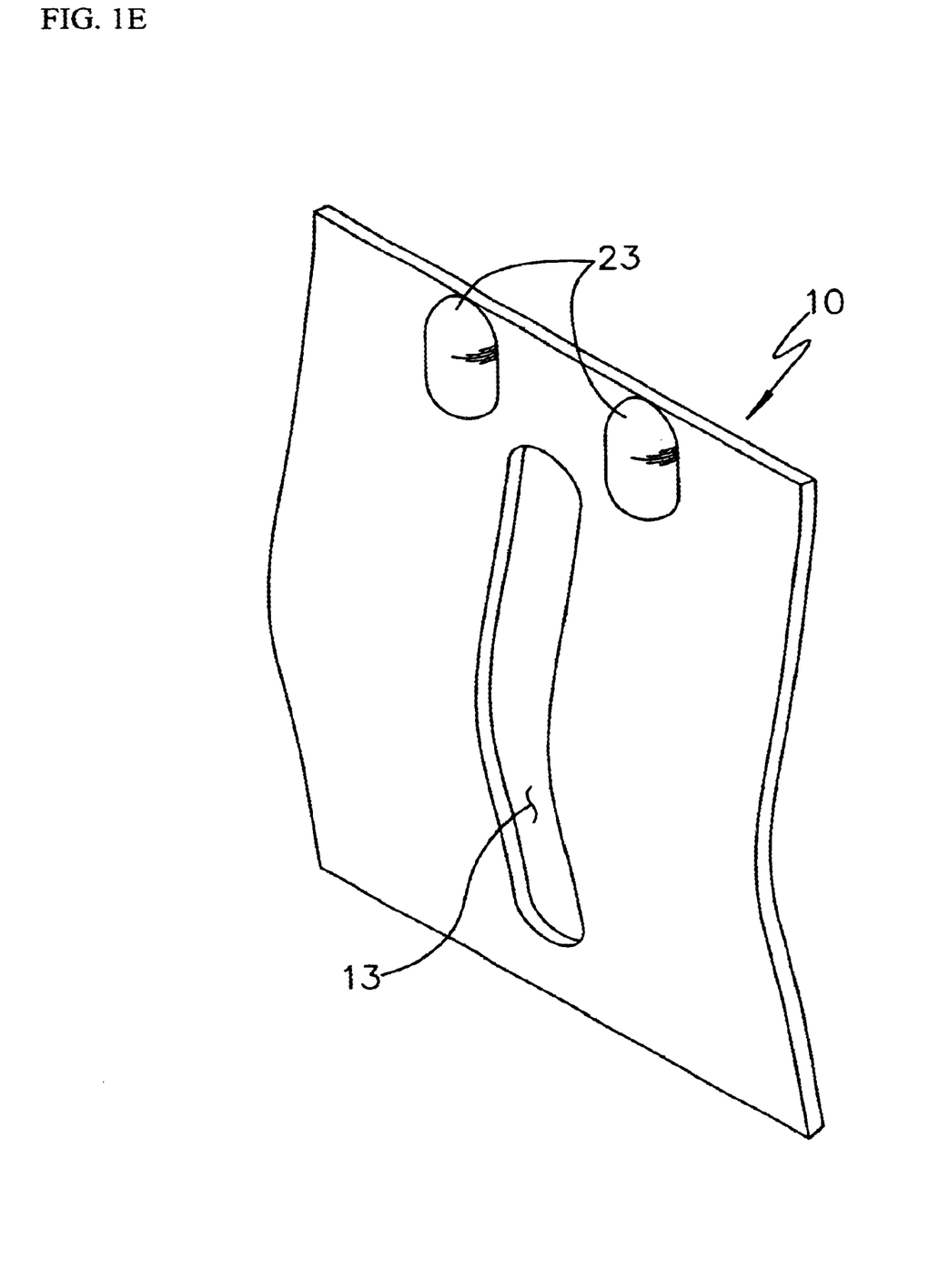
FIG. 1E is a perspective view of the backrest shown in FIG. 1A–1D

Referring to FIG. 1D, which shows a front elevation of the chair described above, shoulder-massaging members 23 are disposed at upper portions on a front surface of the backrest 10. When the user sits on the chair while making the user's back in tight contact with the backrest 10, the shoulder-massaging members 23 stimulate scapular muscles to tenderize the rigidified scapular muscles, thereby soothing the pain at the user's cervical portion, while maintaining the physiological curvature of the user's scapular portion.

Figure 5:
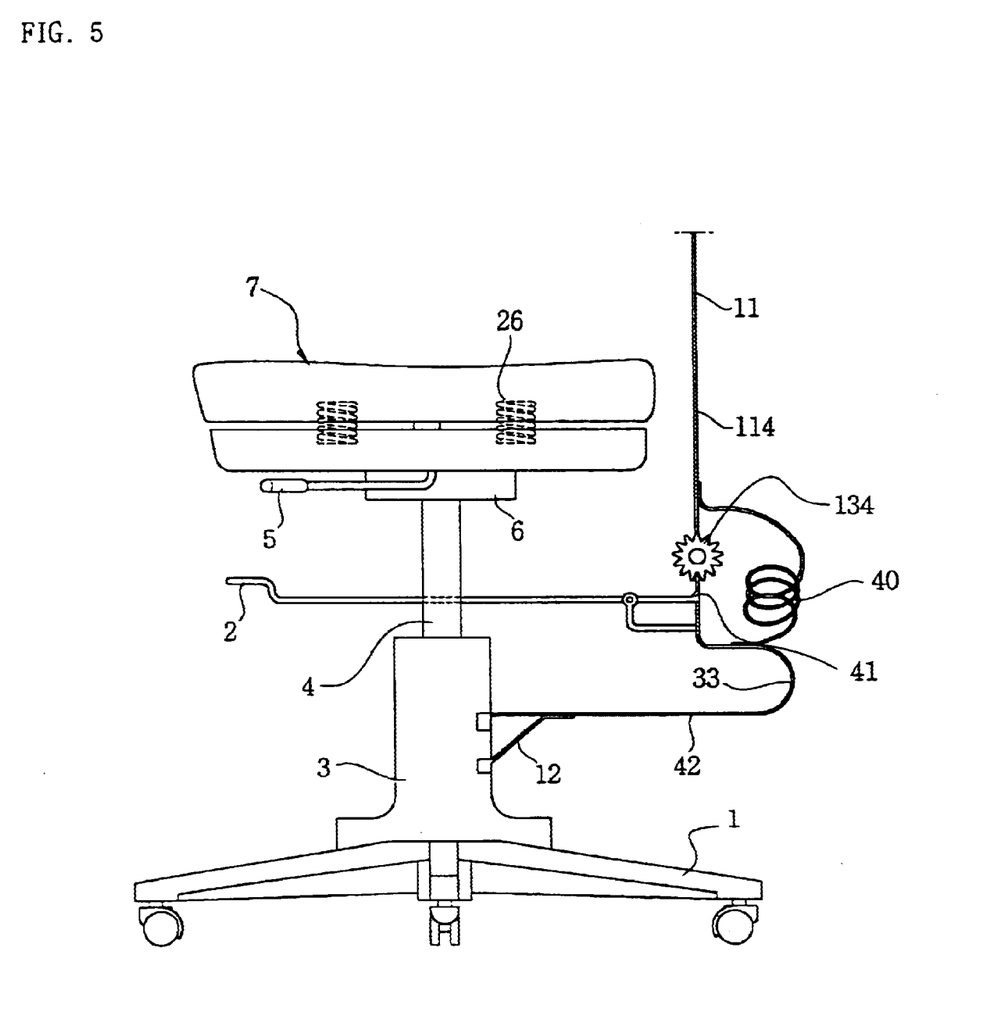
FIG. 5 is a side elevation of a part of another chair for correcting an improper alignment of spinal vertebrae according to another embodiment of the present invention.

FIG. 5 shows another chair according to another embodiment of the present invention, which has a construction similar to that in the prior embodiment excepting several components in relation to the backrest frame 11. That is, the chair according to the present embodiment further includes several elements for maintaining the vertical upper section 114 to be inclined backward and adjusting the inclination of the vertical upper section 114, so as to enable the user of the chair to lean against the backrest 10 while maintaining his or her upper body inclined backward with the adjusted inclination, which means the user can sit on the chair with a more comfortable posture.

In detailed description, a toothed wheel 134 is disposed at a lower portion of the vertical upper section 114, and a backrest adjusting member 2 is arranged under the toothed wheel 134. Further, a second spring 40 is disposed between the vertical upper section 114 and the curved elastic section 33, so as to exert a forward elastic force to the vertical upper section 114. The backrest adjusting member 2 has a grip and a stopper 41 respectively formed at opposite ends of the backrest adjusting member 2. The stopper 41 can be engaged with and disengaged from teeth of the toothed wheel 134 when the user operates the grip to pivot the backrest adjusting member 2 in directions the user wants. When the stopper 41 has been engaged with a tooth of the toothed wheel 134 after the vertical upper section 114 was inclined backward to a predetermined degree the user wants, the vertical upper section 114 is maintained at that location with the adjusted inclination.

Moreover, a supporting bracket 12 is provided between the base cylinder 3 and a lower surface 42 of the horizontal lower section 112, so as to reinforce the joint between the base cylinder 3 and the horizontal lower section 112 and stably support the horizontal lower section 112. A description about other elements, which are the same as those in the preceding embodiment, will be omitted.

As apparent from the above description and drawings, in the chair of the present invention, since the seat 7 and the backrest 10 are separated from each other, they can not only be separately moved but also be simultaneously rotated. Further, likewise in usual chairs, the backrest 10 can be moved up and down corresponding to the user's height in the chair of the invention.

Figure 2A:
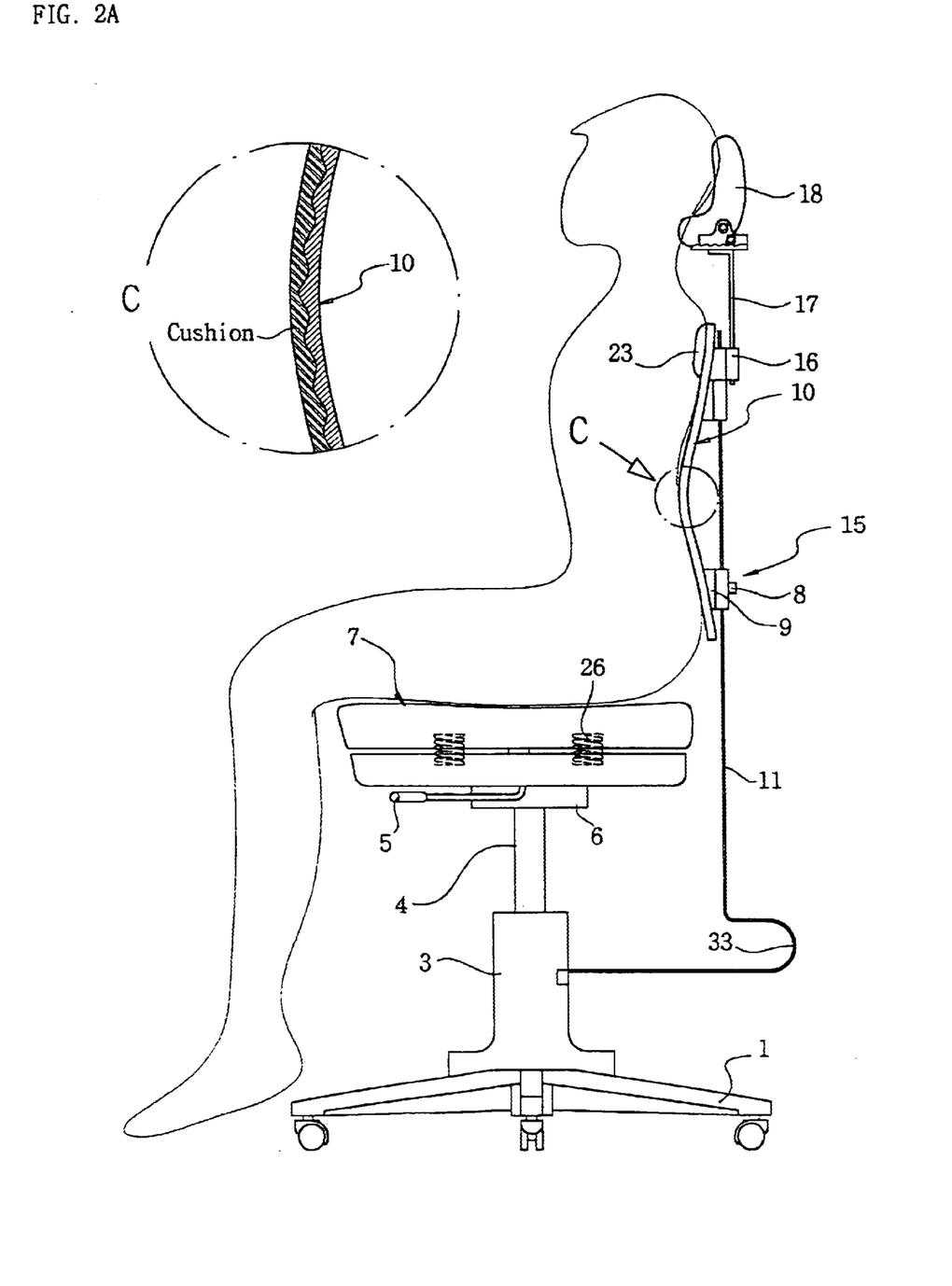
FIGS. 2A and 2B are side views of the chair shown in FIG. 1A, when a seat is respectively at its uppermost position and at its lowermost position, for describing a method for correcting an improper alignment of spinal vertebrae by means of the chair according to another embodiment of the present invention.
Figure 2B:
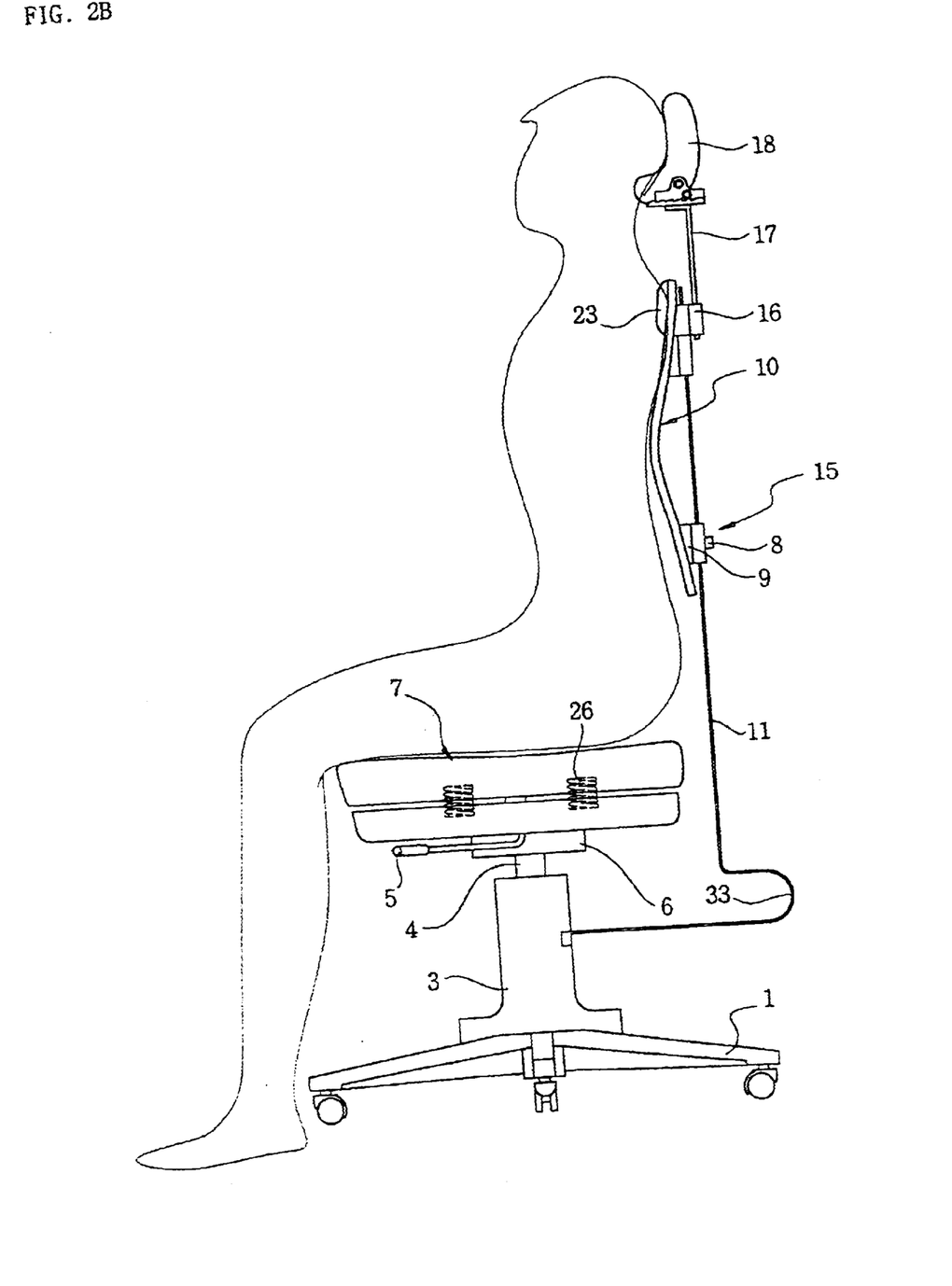

Hereinafter, a method for correcting an improper alignment of spinal vertebrae by means of the chair of the invention according to another embodiment of the present invention will be described with reference to FIGS. 2A and 2B.

First, a user of the chair or a patient is seated on the seat 7 of the chair (step S1). Then, the driving handle 5 and the backrest-elevating system 15 are respectively operated to adjust the heights of the seat 7 and the backrest 10 until the user's back is in tight contact with the backrest 10 (step S2).

Thereafter, the user's neck is inserted between the neck-holding protrusions 19, so that the user's head is seated on the head-resting wall 181 (step S3). In this case, if the user moves his or her head downward, the lower portion of the user's head comes to be caught by the neck-holding protrusions 19. This state is shown in FIG. 2A. Thereafter, the driving handle 5 is operated again to eliminate an upward pressure by the seat-elevating rod 4 for supporting the seat 7 (step S4). Then, the user's lower body rapidly goes downward due to its own weight, and the user's back is relatively slowly lowered due to the tight contact between the user's back and the backrest 10, while the user's head is held in its original position with an unchanged height by the headrest 18 since the lower portion of the user's head is caught by the neck-holding protrusions 19, as shown in FIG. 2B. In other words, the user's twenty-four spinal vertebrae from the cervical vertebrae to the lumbar vertebrae are extended, so that gaps between the spinal vertebrae are naturally enlarged, while the physiological curvature of the spine is maintained. In this case, it is preferred that the eliminated upward pressure by the seat-elevating rod 4 has a value between 10 kg/cm$^2$ and 30 kg/cm$^2$, although it may be changed according to the user's weight When the gaps between the spinal vertebrae are repeatedly enlarged in the way as described above, inflammation at paraspinal tissues and pain due to compression of paraspinal nerves can be naturally reduced and a misalignment of the spinal vertebrae can be corrected. Accordingly, even the herniation of intervertebral disk can be gradually treated by repeating the method of the present invention. Of course, the chair and the method using the chair according to the present invention provide convenience and comfort for not only patients with the herniation of intervertebral disk but also normal healthy users of the chair.

As described above, in a chair for correcting an improper alignment of spinal vertebrae and a method for correcting an improper alignment of spinal vertebrae by means of the chair according to the present invention, when a user of the chair lowers the seat 7 in order to release pain at his or her paraspinal portion, the user's lower body rapidly goes downward, the user's back is relatively slowly lowered, the user's head is held in its original position, while the physiological curvature of the spine is maintained. By repeating such an elongation of the user's upper body, gaps between the spinal vertebrae are repeatedly enlarged and contracted by themselves, so that not only pain due to compression of paraspinal nerves can be naturally reduced and tension of paraspinal muscles can be relieved, but also a misalignment of the spinal vertebrae can be corrected.

In a chair for correcting an improper alignment of spinal vertebrae and a method for correcting an improper alignment of spinal vertebrae by means of the chair according to the present invention, the user's back is properly stimulated by the vertical elongated hole 13 of the backrest 10 when the user's lower body goes downward by lowering the seat 7. This stimulation reinforces the user's paraspinal muscles supporting the user's spine. In result, the user comes to have a distinctive spinal groove representing a strong and healthy spine.

Furthermore, in the chair and the method using the chair according to the invention, the user's cervical vertebrae are also extended and pulled upward when the chair is used. Moreover, the shoulder-massaging members 23 stimulate user's scapular muscles to tenderize the rigidified scapular muscles, thereby soothing the pain at the user's cervical and scapular portions, while maintaining the physiological curvature of the user's scapular portion.

While there have been illustrated and described what are considered to be preferred specific embodiments of the present invention, it will be understood by those skilled in the art that the present invention is not limited to the specific embodiments thereof, and various changes and modifications and equivalents may be substituted for elements thereof without departing from the true scope of the present invention.

What is claimed is:

1. A chair for correcting an improper alignment of spinal vertebrae of a user of the chair, the chair comprising:
    a seat assembly for seating the user on the seat assembly, the seat assembly being operated by the user in such a manner as that the user can adjust a height of the seat assembly,
    the seat assembly including supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle,
    a backrest assembly for supporting a back of the user, the backrest assembly being operated separately from the seat assembly by the user in such a manner that the user can adjust a height of the backrest assembly;
    a headrest assembly for resting a head of the user on the headrest assembly, the headrest assembly being assembled with the backrest assembly; and
    a backrest frame for supporting the backrest assembly and the headrest assembly,
    the backrest frame being fixed to the seat assembly, the backrest assembly moving along the backrest frame when the height of the backrest assembly is adjusted, the backrest frame including a horizontal lower section, a vertical upper section, and a curved elastic section interconnecting the horizontal lower section and the vertical upper section, which are integrated as a single elastic member, the horizontal lower section having one end fixed to the base cylinder.

2. The chair as claimed in claim 1, wherein the seat assembly further comprises a seat bracket fixed to an upper end of the seat-elevating rod and to a lower surface of the seat.

3. The chair as claimed in claim 1, wherein the seat comprises an upper seat plate and a lower seat plate assembled with each other, an assembling groove formed at a central portion of the upper seat plate, an assembling protuberance formed at central portion of the lower seat plate, the assembling groove and the assembling protuberance being engaged with each other, so as to space the upper seat plate and the lower seat plate from each other with a predetermined interval.

4. The chair as claimed in claim 3, wherein spring recesses are formed at four corners of a lower surface of the upper seat plate and at four corners of an upper surface of the lower seat plate, and four first springs are inserted each in each pair of the spring recesses opposed to each other, so that, when the user inclines the user's body in one direction the user wants, the upper seat plate is elastically inclined in said direction corresponding to the user's body.

5. The chair as claimed in claim 1, wherein the backrest assembly comprises a backrest and a backrest-elevating system for moving the backrest up and down along the vertical upper section of the backrest frame.

6. The chair as claimed in claim 5, wherein the backrest assembly further comprises a lower backrest bracket and an upper backrest bracket respectively fixed to lower and upper portions of a rear surface of the backrest, the vertical upper section of the backrest frame being fitted through the lower backrest bracket and the upper backrest bracket in such a manner as that the backrest together with the lower backrest bracket and the upper backrest bracket can be moved up and down along the vertical upper section.

7. The chair as claimed in claim 5, wherein the backrest has a curved shape like the letter "C" in a view from its lateral side, which is complementary to a human spinal curvature and thereby is capable of fitly supporting a human back.

8. The chair as claimed in claim 5, wherein the backrest has a vertical elongated hole formed through a central portion of the backrest, with which a central portion of the human back is to be in contact.

9. The chair as claimed in claim 5, wherein the headrest assembly comprises a headrest, a supporting plate, a carrier plate, a headrest frame, and a headrest frame holding bracket, the headrest frame holding bracket being fixed to a rear surface of the backrest, the headrest frame being held by and extends vertically upward from the headrest frame holding bracket, the supporting plate being fixed to an upper end of the headrest frame, and the carrier plate being disposed on the supporting plate and fixed to the headrest so as to carry the headrest, the carrier plate being capable of sliding forward and backward on the supporting plate.

10. The chair as claimed in claim 9, wherein the supporting plate has a serrated upper surface, and the carrier plate has a carrier plate adjusting lever, which can be operated to be engaged with teeth of the serrated upper surface of the supporting plate, so that the carrier plate can be moved forward and backward and then be firmly held in its location by means of the carrier plate adjusting lever and the serrated upper surface.

11. The chair as claimed in claim 10, wherein the carrier plate adjusting lever can be laterally pulled and pushed when it is engaged with and disengaged from the teeth of the serrated upper surface.

12. The chair as claimed in claim 9, wherein the headrest has a head-resting wall, two neck-holding protrusions protruding forward from lower end portions of the head-resting wall, and a neck-seating portion formed between the two neck-holding protrusions.

13. The chair as claimed in claim 12, wherein the neck-seating portion has such a width as to as to enable a lower portion of the user's head to be caught by the two neck-holding protrusions when the head and a neck of the user have respectively been seated on the head-resting wall and the neck-seating portion.

14. The chair as claimed in claim 9, wherein the carrier plate comprises a headrest pivoting mechanism, which is so fixed to the headrest as to pivot the headrest in a predetermined angle, so that, when the headrest is pivoted backward after the head and the neck of the user are respectively seated on the head-resting wall and the neck-seating portion, the neck-seating portion comfortably supports the neck of the user while maintaining a physiological curvature of the neck and provides the user with a feeling that the neck is slightly pulled upward.

15. The chair as claimed in claim 9, wherein the headrest has a base plate made from hard material, and three laminated layers of cushions surrounding the base plate made from soft materials.

16. The chair as claimed in claim 5, wherein the backrest assembly further comprises shoulder-massaging members disposed at upper portions on a front surface of the backrest, the shoulder-massaging members stimulating scapular muscles of the user to tenderize the scapular muscles.

17. The chair as claimed in claim 5, the chair further comprising a toothed wheel disposed at a lower portion of the vertical upper section, a backrest adjusting member arranged under the toothed wheel, and a second spring disposed between the vertical upper section and the curved elastic section, the backrest adjusting member having a stopper formed at an end of the backrest adjusting member, the second spring exerting a forward elastic force to the vertical upper section, so that, when the stopper has been engaged with a tooth of the toothed wheel after the vertical upper section was inclined backward to a predetermined degree, the vertical upper section is maintained at a predetermined location with an adjusted inclination.

18. The chair as claimed in claim 5, the chair further comprising a supporting bracket provided between the base cylinder and a lower surface of the horizontal lower section, so as to reinforce a joint between the base cylinder and the horizontal lower section and stably support the horizontal lower section.

19. A chair for correcting an improper alignment of spinal vertebrae of a user of the chair, the chair comprising:

a seat assembly including supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle, the seat including an upper seat plate and a lower seat plate assembled with each other, an assembling groove formed at a central portion of the upper seat plate, an assembling protuberance formed at a central portion of the lower seat plate, the assembling groove and the assembling protuberance being engaged with each other, so as to space the upper seat plate and the lower seat plate from each other with a predetermined interval, spring recesses being formed at four corners of a lower surface of the upper seat plate and at four corners of an upper surface of the lower seat plate, and four first springs being inserted each in each pair of the spring recesses opposed to each other, so that, when the user inclines the user's body in one direction the user wants, the upper seat plate is elastically inclined in said direction corresponding to the user's body;

a backrest frame including a horizontal lower section, a vertical upper section, and a curved elastic section interconnecting the horizontal lower section and the vertical upper section, which are integrated as a single elastic member, the horizontal lower section having one end fixed to the base cylinder;

a backrest assembly including a backrest, a lower backrest bracket and an upper backrest bracket respectively fixed to lower and upper portions of a rear surface of the backrest, and a backrest-elevating system for moving the backrest up and down along the vertical upper section of the backrest frame, the vertical upper section of the backrest frame being fitted through the lower backrest bracket and the upper backrest bracket in such a manner as that the backrest together with the lower backrest bracket and the upper backrest bracket can be moved up and down along the vertical upper section, the backrest having a curved shape like a letter "C" in a view from its lateral side, which is complementary to a human spinal curvature, the backrest having a vertical elongated hole formed through a central portion of the backrest, with which a central portion of the human back is to be in contact; and a headrest assembly including a headrest, a supporting plate, a carrier plate, a headrest frame, and a headrest frame holding bracket, the headrest frame holding bracket being fixed to a rear surface of the backrest, the headrest frame being held by and extends vertically upward from the headrest frame holding bracket, the supporting plate being fixed to an upper end of the headrest frame, and the carrier plate being disposed on the supporting plate and fixed to the headrest so as to carry the headrest, the carrier plate being capable of sliding forward and backward on the supporting plate, the supporting plate having a serrated upper surface, the carrier plate having a carrier plate adjusting lever, which can be operated to be engaged with teeth of the serrated upper surface of the supporting plate, so that the carrier plate can be moved forward and backward and then be firmly held in its location by means of the carrier plate adjusting lever and the serrated upper surface, the headrest having a head-resting wall, two neck-holding protrusions protruding forward from lower end portions of the head-resting wall, and a neck-seating portion formed between the two neck-holding protrusions, the neck-seating portion having such a width as to as to enable a lower portion of the user's head to be caught by the two neck-holding protrusions when the head and a neck of the user have respectively been seated on the head-resting wall and the neck-seating portion, the carrier plate further having a headrest pivoting mechanism, which is so fixed to the headrest as to pivot the headrest in a predetermined angle, so that, when the headrest is pivoted backward after the head and the neck of the user are respectively seated on the head-resting wall and the neck-seating portion, the neck-seating portion comfortably supports the neck of the user while maintaining a physiological curvature of the neck and provides the user with a feeling that the neck is slightly pulled upward.

20. A method for correcting an improper alignment of spinal vertebrae of a user of the chair, the chair including a seat assembly, a backrest assembly whose height can be adjusted separately from the seat assembly, a headrest assembly assembled with the backrest assembly, and a backrest frame for supporting the backrest assembly and the headrest assembly, the seat assembly including supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle, the backrest frame including a horizontal lower section, a vertical upper section, and a curved elastic section interconnecting the horizontal lower section and the vertical upper section, which are integrated as a single elastic member, the horizontal lower section having one end fixed to the base cylinder, the backrest assembly moving along the backrest frame when the height of the backrest assembly is adjusted, the backrest assembly having a backrest and a backrest-elevating system, the headrest assembly having a headrest, which includes a head-resting wall, two neck-holding protrusions protruding forward from lower end portions of the head-resting wall, and a neck-seating portion formed between the two neck-holding protrusions, the method comprising the steps of:

(1) seating the user on the seat;

(2) operating the handle and the backrest-elevating system to respectively adjust heights of the seat and the backrest assembly so that a back of the user comes into tight contact with the backrest of the backrest assembly;

(3) inserting a neck of the user between the neck-holding protrusions, so that the head of the user is seated on the head-resting wall; and (4) operating the driving handle again to eliminate an upward pressure by the seat-elevating rod for supporting the seat, so that the user's lower body rapidly goes downward due to its own weight and the user's back is relatively slowly lowered due to the tight contact between the user's back and the backrest, while the user's head is held in its original position with an unchanged height by the headrest since the lower portion of the user's head is caught by the neck-holding protrusions, whereby, the user's twenty-four spinal vertebrae from the cervical vertebrae to the lumbar vertebrae are extended, so that gaps between the spinal vertebrae are naturally enlarged, while the physiological curvature of the spine is maintained.

21. A method for correcting an improper alignment of spinal vertebrae of a user of the chair, the chair including a seat assembly, a backrest assembly whose height can be adjusted separately from the seat assembly, a headrest assembly assembled with the backrest assembly, and a backrest frame for supporting the backrest assembly and the headrest assembly, the seat assembly including supporting legs for generally supporting the seat assembly, a base cylinder integrated with and supported by the supporting legs, a seat-elevating rod movably inserted in the base cylinder, and a seat assembled with and supported by the seat-elevating rod, the seat-elevating rod being elevated by an actuating system housed in the base cylinder, which is operated by a driving handle, the backrest frame including a horizontal lower section, a vertical upper section, and a curved elastic section interconnecting the horizontal lower section and the vertical upper section, which are integrated as a single elastic member, the horizontal lower section having one end fixed to the base cylinder, the backrest assembly moving along the backrest frame when the height of the backrest assembly is adjusted, the backrest assembly having a backrest and a backrest-elevating system, the headrest assembly having a headrest, which includes a head-resting wall, two neck-holding protrusions protruding forward from lower end portions of the head-resting wall, and a neck-seating portion formed between the two neck-holding protrusions, the method comprising the steps of:

(1) seating the user on the seat;

(2) operating the handle and the backrest-elevating system to respectively adjust heights of the seat and the backrest assembly so that a back of the user comes into tight contact with the backrest of the backrest assembly; and (3) operating the driving handle again to eliminate an upward pressure by the seat-elevating rod for supporting the seat, so that a lower portion of the user's back positioned at a lower portion of the backrest rapidly goes downward due to its own weight and an upper portion of the user's back positioned at an upper portion of the backrest is lowered relatively slowly lowered up to a certain point due to the tight contact between the user's back and the backrest, whereby, a lower portion of the user's spinal vertebrae are only extended, so that gaps between the lower portion of the spinal vertebrae are naturally enlarged.

* * * * *